United States Patent
Anderson et al.

(10) Patent No.: US 6,761,911 B2
(45) Date of Patent: Jul. 13, 2004

(54) USE OF CHLORATE ION OR PREPARATIONS THEREOF FOR REDUCTION OF FOOD BORNE PATHOGENS

(75) Inventors: Robin C. Anderson, College Station, TX (US); David J. Nisbet, Bryan, TX (US); Larry H. Stanker, Livermore, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 9 days.

(21) Appl. No.: 10/264,101

(22) Filed: Oct. 3, 2002

(65) Prior Publication Data

US 2003/0039703 A1 Feb. 27, 2003

Related U.S. Application Data

(63) Continuation of application No. 09/354,446, filed on Jul. 15, 1999, now Pat. No. 6,475,527.

(51) Int. Cl.$^7$ ........................ A01N 59/00; A01N 57/16; A61K 33/20
(52) U.S. Cl. ........................ 424/662; 424/438; 424/439; 424/441; 424/442; 424/617; 424/661; 424/665; 514/867; 426/807
(58) Field of Search ........................ 424/662, 438–439, 424/441–442, 617, 661, 665, 718; 514/867, 81, 129, 557, 574; 426/807, 332, 335, 532

(56) References Cited

PUBLICATIONS

VETU Abstract, accession No. 1993–60715; abstracting, Pardue, S. L. et al., "Influence of a novel oxy–halogen compound on early growth and nitrogen retention of broiler chickens challenged with Salmonella," Poult. Sci., vol. 72(2), 1993, pp. 259–26.*

* cited by examiner

*Primary Examiner*—John Pak
(74) *Attorney, Agent, or Firm*—John D. Fado; Randall E. Deck

(57) ABSTRACT

The invention provides a method and compositions for controlling food borne enteric bacterial pathogens in animals. Populations of enteropathogenic bacteria may be substantially reduced or eliminated by treatment of animals with an effective amount of the compound $X_m(ClO_3)_n$, wherein X is a cationic moiety and m and n are independently selected from integers necessary to provide a net valency of 0. The compounds may be administered orally, providing a reduction in the populations of the enteropathogenic bacteria in the alimentary tract of the animal, or they may be applied externally onto the animal to reduce the populations of any such bacteria which may be present as contaminants on the surface of the animal. The method and compositions are particularly useful for the control of Salmonella species, enteropathogenic *Escherichia coli*, and Clostridia species.

3 Claims, No Drawings

USE OF CHLORATE ION OR PREPARATIONS THEREOF FOR REDUCTION OF FOOD BORNE PATHOGENS

This application is a continuation application Ser. No. 09/354,446, filed Jul. 15, 1999, now U.S. Pat. No. 6,475,527 which is incorporated by reference herein.

BACKGROUND OF THE INVENTION

1. Field of the Invention

This invention relates to a process for the control of enteric bacterial pathogens in animals using chlorate ion.

2. Description of the Prior Art

Despite the efforts of researchers and public health agencies, the incidence of human infections from enteropathogenic bacteria such as Salmonella, *E. coli*0157: H7, and Campylobacter has increased over the past 20 years. For example, the number of actual reported cases of human Salmonella infection exceeds 40,000 per year. However, the Communicable Disease Center estimates that the true incidence of human Salmonella infections in the U.S. each year may be as high as 2 to 4 million. The USDA Economic Research Service has recently reported that the annual cost of the food borne illnesses caused by six common bacterial pathogens, Campylobacter spp., *Clostridium perfringens, Escherichia coli* 0157: H7, *Listeria monocytogenes, Salmonella spp.*, and *Staphylococcus aureus*, ranges from 2.9 billion to 6.7 billion dollars (Food Institute Report, USDA, AER, December, 1996). In addition to the impact of enteric pathogens on human health, many of these bacteria also cause significant infections in animals. For example, Salmonella infections in swine alone cost the United States swine industry more than 100 million dollars annually (Schwartz, 1990, "Salmonellosis in Midwestern Swine", In: Proceedings of the United States Animal Health Assoc., pp. 443–449).

Animal food products remain a significant source of human infection by these pathogens. Contamination of meat and poultry with many bacterial food-borne pathogens, including the particularly onerous pathogens *Campylobacter spp., Escherichia coli* 0157:H7, and *Salmonella spp.*, often occurs as a result of exposure of the animal carcass to ingesta and/or fecal material during or after slaughter. Any of the above-mentioned pathogens can then be transmitted to humans by consumption of meat and poultry contaminated in this manner.

Preharvest control of enteropathogenic bacteria is a high priority to the food industry. However, few products have been developed to facilitate such efforts. Currently, preharvest pathogen control within the poultry industry is accomplished through use of competitive exclusion cultures or probiotics. In fact, at this time, only one such product, developed by Nisbet et al. of the USDA Agricultural Research Service (U.S. Pat. No. 5,478,557) and sold under the trademark PREEPMT (Milk Specialties Biosciences, Dundee, Il.), is available commercially in the United States. Moreover, the administration of competitive exclusion cultures is preferably targeted to very young animals. Immune lymphokines (ILK) have also been recently developed for protecting poultry from colonization with enteric pathogens as described by ziprin et al. (1989, Poult. Sci., 68:1637–1642), McGruder et al. (1993, Poult. Sci., 72:2264–2271), Ziprin et al. (1996, Avian Dis., 40:186–192), and Tellez et al. (1993, Avian Dis., 37:1062–1070), and more recently by Kogut et al. (U.S. Pat. Nos. 5,891,443 and 5,691,200). However, despite these advances, the need persists for technologies for controlling enteric pathogens in animals, and particularly for the treatment of animals immediately prior to slaughter.

SUMMARY OF THE INVENTION

We have now discovered a method and compositions for controlling food borne enteric bacterial pathogens in animals. Populations of enteropathogenic bacteria may be substantially reduced by treatment of animals with an effective amount of a compound of the formula $X_m(ClO_3)_n$, wherein X is a cationic moiety and m and n are independently selected from integers necessary to provide a net valency of the compound of 0. The compounds may be administered orally, providing a reduction in the populations of the enteropathogenic bacteria in the alimentary tract of the animal, or they may be applied externally onto the animal to reduce the populations of any such bacteria which may be present as contaminants on the surface of the animal. The method and compositions are particularly useful for the control of Salmonella species, enteropathogenic *Escherichia coli*, and some Clostridia species.

In accordance with this discovery, it is an object of this invention to provide a method for controlling food borne enteropathogenic bacteria in animals.

Another object of this invention is to provide a method for controlling enteropathogenic bacteria in the gastrointestinal tract of animals without adversely effecting populations of commensal or beneficial bacteria.

Yet another object of this invention is to provide a method for significantly reducing the populations of enteropathogenic bacteria in meat producing animals prior to slaughter.

Other objects and advantages of this invention will become readily apparent from the ensuing description.

DETAILED DESCRIPTION OF THE INVENTION

Compounds of the formula $X_m(ClO_3)_n$, wherein X is a cationic moiety and m and n are independently selected from integers necessary to provide a net valency of the compound of 0, and which compounds release free chlorate ion ($ClO_3^-$) while in solution, are effective for controlling or killing several different enteropathogenic bacteria. A variety of cationic moieties are suitable for use herein, and examples thereof include but are not limited to H, alkali-metals, alkaline-earth metals, transition metals, and cationic radicals such as ammonium groups. Generally, chloric acid and salts thereof (i.e., chlorates) are preferred for use herein, with sodium chlorate and potassium chlorate being particularly preferred.

Enteropathogenic bacteria which may be controlled with $X_m(ClO_3)_n$ include but are not limited to Salmonella species, enteropathogenic *Escherichia coli* 0157:H7, and some Clostridia species. Without wishing to be bound by theory, these pathogens all possess respiratory nitrate reductases which are capable of reducing the chlorate ion, which is dissociated from these compounds when they are in solution, to the cytotoxic chlorite ion in an anaerobic environment. Consequently, only those bacteria which possess a respiratory nitrate reductase are effected by this invention (i.e., killed by chlorite ion). It is also envisioned that Campylobacter species may be subject to control using the $X_m(ClO_3)_n$ of this invention. Because relatively few other genera and species of bacteria contain these enzymes, including most commensal and mutualistic (beneficial) bacteria, other non-pathogenic bacteria are generally not effected.

Depending upon the route of treatment, the $X_m(ClO_3)_n$ compounds are effective for reducing the populations of the enteropathogenic bacteria within the gastrointestinal tract of animals when administered orally, or for reducing the populations of these bacteria which may be present as contaminants on the surfaces of the animal when applied externally. The process may be used for the treatment of a wide variety of animals, including humans. However, without being limited thereto, the process is preferably used for the treatment of meat-producing animals, such as bovine, fowl, porcine, ovine, and equine, and particularly cattle, chickens, turkeys, ducks, quail, geese, pigs, and sheep.

In a first preferred embodiment, the $X_m(ClO_3)_n$ compounds are administered orally to the subject animal for reducing (killing) populations of the enteropathogenic bacteria in the gastrointestinal tract. Typically, the compounds will be introduced into the alimentary tract by combining with the animal's feed or water, followed by oral ingestion thereof. However, it is also understood that the compounds may be administered separately or in combination with other conventional treatments.

In an alternative preferred embodiment, the $X_m(ClO_3)_n$ compounds are applied onto meat producing animals for reducing populations of the enteropathogenic bacteria on its head, torso and/or appendages. It is generally recognized that the hides, feathers, hair, feet and/or hoofs of such animals often become contaminated with fecal material, and may subsequently serve as sources for contamination with enteropathogenic bacteria. During slaughter, the carcasses or meat of the animals may become contaminated when contacted with any of these parts of the animal. In this embodiment, the compounds are preferably applied as a spray on the animal, although they may also be applied using other techniques such as dipping, or dusting.

Treatment with the $X_m(ClO_3)_n$ compounds may occur at any time during the life of the animal. However, in the preferred embodiment, meat-producing animals are treated shortly before they are to be slaughtered, thereby reducing or eliminating the number of enteropathogenic bacteria present in the gut of each treated animal and reducing the incidence of contamination of the carcass or meat during slaughterhouse processing. As a practical matter, the compounds will be orally administered to the animals just prior to shipment to slaughter facilities, or immediately upon arrival at such facilities. This will typically be within about 96 hours, particularly within about 48 hours, prior to slaughter. External application of the animals with the compounds will preferably occur within the same time period.

The $X_m(ClO_3)_n$ compounds are administered in an amount effective to control the population(s) of the target enteropathogenic bacteria in animals. An effective amount is defined herein as that amount which will significantly reduce or eliminate the population(s) of the target enteropathogenic bacteria, and/or reduce the incidence of infection by these bacteria, in a treated animal in comparison to untreated control animal. A reduction of incidence of infection may be demonstrated by a significant reduction in the number of animals infected or the severity or pathogenicity of infection, in comparison with untreated control animal. It is also understood that a reduction of incidence of infection may be demonstrated by a significant inhibition of intestinal, ruminal, or cecal colonization by the microorganism (as indicated by one or more of reducing pathogen shedding, reducing the average pathogen concentration, or lowering the percentage of animals colonized) in comparison with untreated controls. Suitable amounts may be readily determined by the practitioner skilled in the art, and will vary with the specific subject animal, its age, size, and physiological condition. Without being limited thereto, suitable doses should provide a concentration of $ClO_3^-$ which is greater than or equal to about 0.01 mM within the lumen of the intestinal tract or gut of the treated animal, although amounts providing concentrations greater than or equal to 0.1 mM, and particularly greater than or equal to 1.0 mM, are preferred. It is generally envisioned that control of enteropathogenic bacteria in fowl may require lower concentrations of the chlorate ion in the gut of the animal, while ruminant animals such as cattle may require higher concentrations between about 1 to 5 mM. However, the upper limit of the chlorate ion concentration may be much higher and will depend on the levels tolerated by the subject animal. For example, higher dosages providing intraluminal chlorate ion concentrations greater than 50 mM, and even up to 250 mM, may be used in many instances such as in fowl and/or ruminants.

Although pure or substantially pure $X_m(ClO_3)_n$ compounds may be administered to the animals directly, in an optional yet preferred embodiment they are provided in the animal's feed or water. Alternatively, the compounds may be further formulated with a conventional inert carrier or pharmaceutically acceptable carrier to facilitate administration. For example, without being limited thereto, all or a portion of the compounds may be encapsulated using techniques conventional in the art, including but not limited to encapsulation in alginate gels. When treating ruminant animals, a portion of the compounds is preferably encapsulated to allow higher concentrations of chlorate ion to reach the hindgut of the animal, while still allowing for control of pathogenic bacteria in the rumen. The compounds may also be formulated with lactose or skim milk, or combined with a small amount of feed or water for use as a premix. Adjuvants conventional in the art for the treatment of the animals, including those for the treatment of enteropathogens, may also be formulated with the compounds. Suitable adjuvants include but are not limited to vaccines, antitoxins, deworming agents, or therapeutic antibiotics. Non-therapeutic levels of antibiotics may also be administered to the animals as is conventional in the art.

In a particularly preferred embodiment, when controlling enteropathogenic bacteria in the gut of the animal, small amounts of nitrate are administered to the animal shortly prior to or at approximately the same time as the $X_m(ClO_3)_n$. Because respiratory nitrate reductases are typically expressed under anaerobic conditions in the presence of nitrate, administration of nitrate ion in this manner ensures that maximum levels of enzyme are induced by the target bacteria. However, it is understood that addition of nitrate is optional as the added chlorate as well as any nitrates in the diet of the animal will also induce enzyme expression. A variety of nitrates are suitable for use herein and include but are not limited to nitrate salts such as sodium or potassium nitrate, or ammonium nitrate. The amount of nitrate administered is not critical but should be effective to induce expression of the respiratory nitrate reductase in the target bacteria. Generally, nitrate concentrations between about 0.1 to 10.0 mM, and particularly between about 1 to 10 mM, are preferred.

In another preferred embodiment, substrates effective as hydrogen donors for the respiratory nitrate reductases may also be orally administered to the animal. As with the nitrates described above, hydrogen donors are preferably administered to the animal shortly prior to or at approximately the same time as the $X_m(ClO_3)_n$. A number of compounds are suitable for use as hydrogen donors herein, including compounds which function directly as hydrogen donors such as formate, NADH, lactate, succinate, and glycerol-3-phosphate, as well as fermentable substrates which indirectly function as hydrogen donors as they are oxidized to metabolic products which are hydrogen donors for the respiratory nitrate reductase. However, lactate and formate are generally preferred for use herein.

The following examples are intended only to further illustrate the invention and are not intended to limit the scope of the invention which is defined by the claims.

EXAMPLE 1

Demonstration of the Efficacy of Chlorate in Vivo

In order to assess both the efficacy of chlorate against enteropathogens and its toxicity against cattle, relatively large doses of sodium chlorate (30 mM) were intraruminally administered to cattle. Experiments were conducted both with cattle allowed continuous access to an alfalfa hay-:flaked corn (9:1) diet, and with cattle that were fasted 24 hours prior to and after chlorate treatment. Concentrations of $E.$ $coli$ in the ruminal contents and in feces collected from the test animals were determined by viable cell counts on MacConkey agar plates. The results are shown in Table 1, with the concentrations of $E.$ $coli$ expressed as log base 10. As shown therein, for both fasted and non-fasted animals, ruminal $E.$ $coli$ concentrations decreased only slightly from prechlorate levels by 10 hours after chlorate administration, but after 24 hours the decrease in the concentration was significantly greater. In contrast, ruminal $E.$ $coli$ concentrations from untreated control animals not given chlorate increased over the same time period. Surprisingly, the addition of chlorate exhibited a much greater effect on the fecal concentrations of $E.$ $coli$, with concentrations in the treated animals being greatly reduced in 24 hours relative to the untreated controls. These results suggest that effective quantities of the chlorate ion have passed to the lower gut, and that the treatment should be effective for both ruminant and monogastric species.

TABLE 1

Effect of chlorate treatment on ruminal and fecal EC concentrations.

| Time Post treatment (h) | Fasted | | Nonfasted | |
|---|---|---|---|---|
| | Treated | Untreated | Treated | Untreated |
| Mean ± SD (n = 2) ruminal EC concentration (log base 10 CFU/g) | | | | |
| 0 | 3.62 ± 2.29 | 2.59 ± 0.36 | 3.66 ± 1.76 | 3.81 ± 1.28 |
| 10 | 3.27 ± 3.21 | 4.16 ± 0.63 | 2.22 ± 3.14 | 4.10 ± 1.98 |
| 24 | 2.40 ± 0.20 | 4.63 ± 0.35 | 2.28 ± 1.38 | 2.83 ± 0.25 |
| Mean ± SD (n = 2) fecal EC concentration (log base 10 CFU/g) | | | | |
| 0 | 5.29 ± 0.24 | 6.28 ± 0.84 | 5.19 ± 1.68 | 5.37 ± 0.70 |
| 24 | 2.33 ± 1.24 | 5.80 ± 1.64 | 2.65 ± 1.91 | 5.64 ± 0.42 |

EXAMPLE 2

Demonstration of Efficacy in Vitro

Ruminal contents, a potential reservoir of pathogenic bacteria, were collected from a cannulated cow maintained on pasture (predominantly rye grass), mixed 1:1 with a phosphate buffer (pH 6.2 r 6.8) supplemented with cellobiose, glucose, soluble starch, and xylose (1% wt/vol each), and inoculated with either a novobiocin and nalidixic acid resistant strain of $E.$ $coli$ O157:H7 (5.9 $\log_{10}$ colony forming units/ml) or Salmonella typhimurium DT104 (5.5 $\log_{10}$ colony forming units/ml). These inoculated ruminal fluids were incubated anaerobically at 39° C. in duplicate with or without 5 mM sodium chlorate for 24 hours. Sodium nitrate (2.5 mM) was also added to some of the samples containing chlorate and $S.$ $typhimurium.$ $E.$ $coli$ O157:H7 concentrations ($\log_{10}$ cfu/ml) were determined from colony counts on MacConkeys agar containing 25 ug/ml novobiocin and 20 $\mu$g/ml nalidixic acid, and $S.$ $typhimurium$ concentrations were determined from colony counts on Brilliant Green agar containing 25 $\mu$g/ml each of novobiocin and chloramphenicol.

Without added chlorate, $E.$ $coli$ concentrations declined slightly from 5.9 to 5.7 and 5.1 ($\log_{10}$ cfu/ml) after 24 hours incubation at pH 6.2 and 6.8, respectively. In contrast, in cultures with added chlorate, $E.$ $coli$ concentrations decreased below the level of detection, to less than 10 cfu/ml (less than 1 $\log_{10}$ cfu/ml), after only 6 hours of incubation. Chlorate addition had little effect on the most probable number of culturable anaerobes.

Concentrations of $S.$ $typhimurium$ declined to 4.1 $\log_{10}$ cfu/ml without added chlorate after 24 hours. In contrast, the $S.$ $typhimurium$ concentration was reduced to 1.7 $\log_{10}$ cfu/ml after incubation with chlorate for 24 hours. The reduction in the Salmonella concentration was even more dramatic when nitrate was added with the chlorate, with the $S.$ $typhimurium$ concentration declining to less than 1 $\log_{10}$ cfu/ml after 24 hours.

It is understood that the foregoing detailed description is given merely by way of illustration and that modifications and variations may be made therein without departing from the spirit and scope of the invention.

We claim:

1. A method for controlling bacterial enteropathogens in an animal comprising treating a meat-producing animal within about 96 hours prior to slaughter with a composition comprising $X_m(ClO_3)_n$ in an amount effective to inhibit growth of enteropathogenic bacteria, wherein X is a cationic moiety and m and n are independently selected from integers necessary to provide a net valency of 0, which said composition is not toxic to non-pathogenic bacteria which lack respiratory nitrate reductases capable of reducing chlorate ion, and further wherein said amount is effective to achieve a concentration of $ClO_3$ of greater than or equal to about 0.01 mM within the lumen of the gut of said animal.

2. A method for controlling bacterial enteropathogens in an animal comprising oral administering to said animal a composition comprising $X_m(ClO_3)_n$ in an amount effective to inhibit growth of enteropathogenic bacteria, wherein X is a cationic moiety and m and n are independently selected from integers necessary to provide a net valency of 0, which said composition is not toxic to non-pathogenic bacteria which lack respiratory nitrate reductases capable of reducing chlorate ion, and further wherein said amount is effective to achieve a concentration of $clo_3^-$ of greater than or equal to about 0.01 mM within the lumen of the gut of said animal.

3. A method for controlling bacterial enteropathogens in an animal comprising treating said animal with a composition comprising $X_m(ClO_3)_n$ in an amount effective to inhibit growth of enteropathogenic bacteria, wherein X is a cationic moiety and m and n are independently selected from integers necessary to provide a net valency of 0, which said composition is not toxic to non-pathogenic bacteria which lack respiratory nitrate reductases capable of reducing chlorate ion, and further wherein said animal is selected from the group consisting of fowl, equine, and humans.

* * * * *